United States Patent [19]
Kume et al.

[11] Patent Number: 4,729,784
[45] Date of Patent: Mar. 8, 1988

[54] 1-(1,4-BENZOXAZIN-3-ON-6-YL)-DIALKYL-MALEIMIDES AND USE AS HERBICIDES

[75] Inventors: Toyohiko Kume; Toshio Goto; Atsumi Kamochi; Naoko Yamaguchi; Akihiko Yanagi, all of Tokyo; Hidenori Hayakawa, Kanagawa; Shigeki Yagi, Tokyo, all of Japan

[73] Assignee: Nihon Tokushu Noyaku Seizo K.K., Tokyo, Japan

[21] Appl. No.: 65,443

[22] Filed: Jun. 23, 1987

[30] Foreign Application Priority Data
Jul. 7, 1986 [JP] Japan .................. 61-157890

[51] Int. Cl.$^4$ .................. A01N 43/84; C07D 413/04
[52] U.S. Cl. .................. 71/95; 544/69; 544/105
[58] Field of Search .................. 544/69, 105; 71/95

[56] References Cited
U.S. PATENT DOCUMENTS
4,640,707 2/1987 Nagano et al. .................. 544/105 X FOREIGN PATENT DOCUMENTS
0170191 2/1986 European Pat. Off. .
0170842 2/1986 European Pat. Off. .
61-30586 12/1986 Japan .

Primary Examiner—Richard L. Raymond
Attorney, Agent, or Firm—Sprung, Horn, Kramer & Woods

[57] ABSTRACT

Novel dialkylmaleimides of the formula (I)

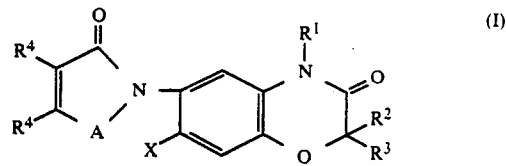

and the use of the novel compounds as herbicides.

11 Claims, No Drawings

1-(1,4-BENZOXAZIN-3-ON-6-YL)-DIALKYL-MALEIMIDES AND USE AS HERBICIDES

The present invention relates to novel dialkylmaleimides, to processes for their preparation and to their use as herbicides.

It has already been disclosed that certain tetrahydrophthalimides have herbicidal activities. (See Japanese patent Laid-open No. 30586/1986)

There have now been found novel dialkylmaleimides of the formula (I)

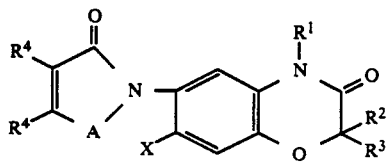 (I)

In the formula:
A represents

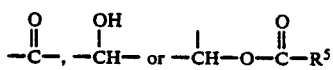

in which $R^5$ represents an alkyl or aryl gorup, $R^1$ represents a hydrogen atom, an alkyl group, an alkenyl group, an alkynyl group, an aralkyl group, an alkoxyalkyl group, a cyano alkyl group, a trialkylsilylalkyl group, an alkylthioalkyl group or the group

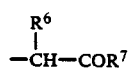

in which $R^6$ represents a hydrogen atom or an alkyl group and $R^7$ represents an alkoxy, cycloalkoxy, haloalkoxy, alkylamino, dialkylamino, N-alkyl-N-arylamino or trialkylsilylalkoxy group, $R^2$ represents a hydrogen atom or an alkyl, aryl or aralkyl group, $R^3$ represents a hydrogen atom or an alkyl group, $R^4$ represents an alkyl group, and X represents a hydrogen atom, a halogen atom or an alkyl group.

The compounds of the formula (I) are obtained by a process in which, (a) in the case where A is

compounds of the formula (II)

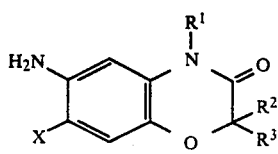 (II)

wherein $R^1$, $R^2$, $R^3$ and X are as defined above, are reacted with compounds of the formula (III)

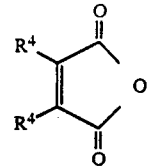 (III)

wherein $R^4$ is as defined above, in the presence of inert solvents, or (b) in the case where A is

compounds of the formula (I-a)

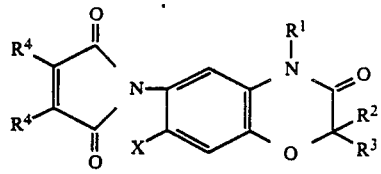 (I-a)

wherein $R^1$, $R^2$, $R^3$, $R^4$ and X are as defined above, are reacted with a reducing agent, in the presence of inert solvents, or (c) in the case where A is

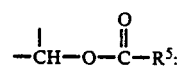

compounds of the formula (I-b)

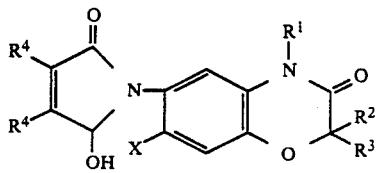 (I-b)

wherein $R^1$, $R^2$, $R^3$, $R^4$ and X are as defined above, are reacted with compounds of the formula (IV)

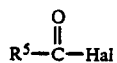 (IV)

wherein $R^5$ is as defined above, and Hal represents a halogen atom, or with compounds of the formula (V)

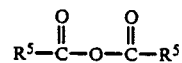 (V)

wherein $R^5$ is as defined above, in the presence of inert solvents and if appropriate, in the presence of acid binders.

The novel dialkylmaleimides exhibit powerful herbicidal properties.

Surprisingly, the dialkylmaleimides according to the invention exhibit not only a substantially greater herbicidal action than those known from aforesaid prior art, but also a favorable compatibility with crops, without phytotoxicity.

Preferably, in the formula (I) representing the compounds of this invention,

A represents

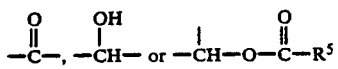

in which R⁵ represents an alkyl group having 1 to 4 carbon atoms or a phenyl group, R¹ represents a hydrogen atom, an alkyl group having 1 to 4 carbon atoms, an alkenyl group having 2 to 4 carbon atoms, an alkynyl group having 2 to 4 carbon atoms, a benzyl group, an alkoxyalkyl group having 2 to 6 carbon atoms in total, a cyanomethyl group, a trimethylsilylmethyl group, an alkylthioalkyl group having 2 to 6 carbon atoms in total or the group

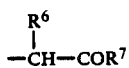

in which R⁶ represents a hydrogen atom or an alkyl group having 1 to 2 carbon atoms and R⁷ represents an alkoxy group having 1 to 4 carbon atoms, a cycloalkoxy group having 3 to 7 carbon atoms, a haloalkoxy group having 1 to 4 carbon atoms, an alkylamino or dialkylamino group having 2 to 6 carbon atoms in total, an N-(C₁-C₄)alkyl-N-phenylamino group, or a trimethylsilylmethoxy group, R² represents a hydrogen atom, an alkyl group having 1 to 6 carbon atoms, a phenyl group or a benzyl group, R³ represents a hydrogen atom or an alkyl group having 1 to 4 carbon atoms, R⁴ represents an alkyl group having 1 to 4 carbon atoms, and X represents a hydrogen atom, a fluorine atom, a chlorine atom, a bromine atom, a methyl group or an ethyl group.

Especially preferably, in the formula (I) A represents

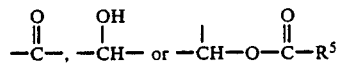

in which R⁵ represents a methyl, ethyl or phenyl group,

R¹ represents a hydrogen atom, a methyl, ethyl, propyl, allyl, propargyl, benzyl, methoxymethyl, cyanomethyl, trimethylsilylmethyl, methylthiomethyl or 2-ethylthioethyl group or the group

in which R⁶ represents a hydrogen atom or a methyl group and R⁷ represents a methoxy, ethoxy, cyclopentyloxy, cyclohexyloxy, trifluoroethoxy, isoproylamino, dimethylamino, N-methyl-N-phenylamino or trimethylsilylmethoxy group, R² represents a hydrogen atom or a methyl, ethyl, n-propyl, n-butyl, n-hexyl, phenyl or benzyl group, R³ represents a hydrogen atom or a methyl group, R⁴ represents a methyl group, and X represents a hydrogen or fluorine atom.

Specific examples of the compounds of the formula (I) provided by this invention particularly include
1-[4-propyl-2H-1,4-benzoxazin-3(4H)-on-6-yl]-3,4-dimethyl-2,5-dioxo-2,5-dihydropyrrole,
1-[4-allyl-2H-1,4-benzoxazin-3(4H)-on-6-yl]-3,4-dimethyl-2,5-dioxo-2,5-dihydropyrrole,
1-[4-propargyl-2H-1,4-benzoxazin-3(4H)-on-6-yl]-3,4-dimethyl-2,5-dioxo-2,5-dihydropyrrole,
1[4-propyl-2-methyl-1,4-benzoxazin-3(4H)-on-6-yl]-3,4-dimethyl-2,5-dioxo-2,5-dihydropyrrole, and
1-[4-propyl-2,2-dimethyl-1,4-benzoxazin-3(4H)-on-6-yl]-3,4-dimethyl-2,5-dioxo-2,5-dihydropyrrole.

If in process (a), 6-amino-4-propyl-2H-1,4-benzoxazin-3(4H)-one and 2,3-dimethylmaleic anhydride, for example, are used as starting materials, the reaction is shown by the following scheme:

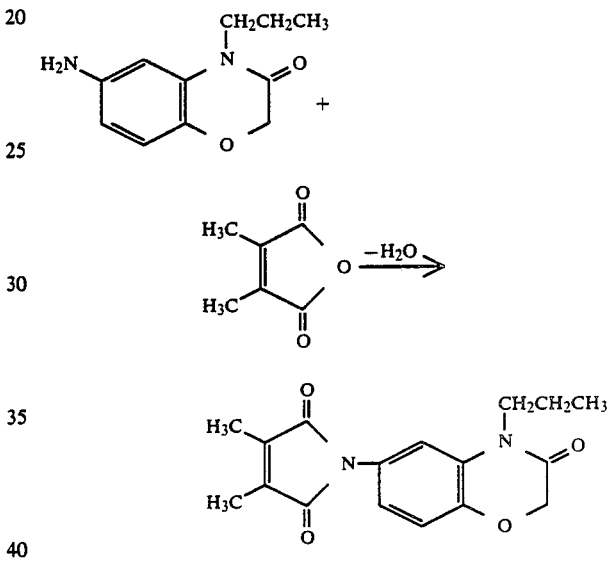

If in process (b), 1-[4-propyl-2H-1,4-benzoxazin-3(4H)-on-6-yl]-3,4-dimethyl-2,5-dioxo-2,5-dihydropyrrole and sodium borohydride, for example, are used as starting materials, the reaction is shown by the following scheme:

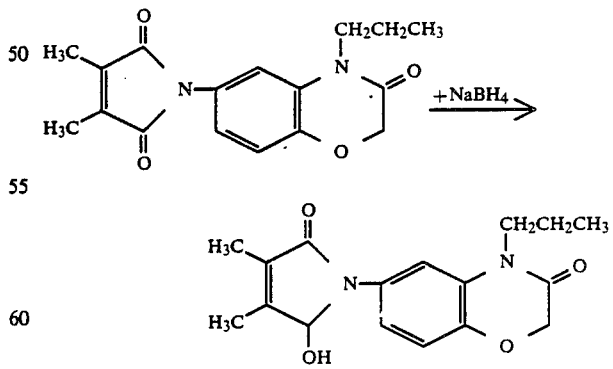

If in process (c), 1-[4-propyl-2H-1,4-benzoxazin-3(4H)-on-6-yl]-3,4-dimethyl-2-hydroxy-5-oxo-2,5-dihydropyrrole and acetyl chloride, for example, are used as starting materials, the reaction is shown by the following scheme:

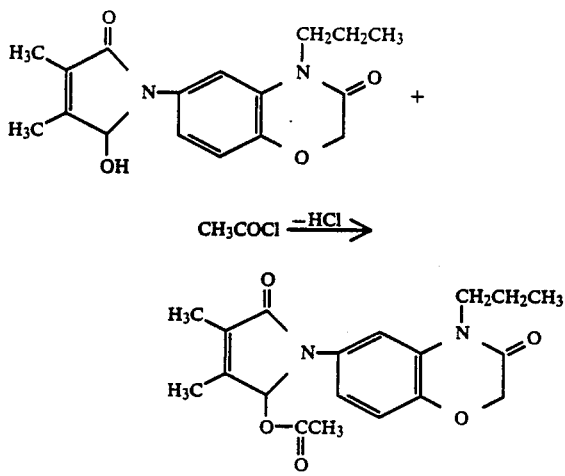

In process (a), the compound of formula (II) as a starting material means one based on the above definitions of $R^1$, $R^2$, $R^3$ and X, preferably one based on the preferred definitions of these symbols.

The compound of formula (II) include, for example, the known compounds described in Japanese Laid-Open Patent Publications Nos. 30586/1986 and 76486/1986.

Generally, the compound of formula (II) can be easily obtained by reducing the corresponding 6-nitro-4-substituted-1,4-benzoxazinone in accordance with the method described in the above-cited Japanese Laid-Open Patent Publication No. 30586/1986.

The 6-nitro-4-substituted-1,4-benzoxazinone can also be produced easily by the method of Japanese Laid-Open Patent Publication No. 30586/1986.

The 6-nitro-4-substituted-1,4-benzoxazinone can be easily produced from 2-amino-4-nitrophenol as a starting material in accordance with the methods described in Japanese Laid-Open Patent Publication No. 125529/1974 and Synthesis, 1984, page 851.

6-Amino-4-propyl-2H-1,4-benzoxazin-3(4H)-one may be cited as a specific example of the compounds of the formula (II).

The compounds of the formula (III) which is likewise a starting material means one based on the definition of $R^4$, preferably one based on the preferred definition of $R^4$.

The compounds of the formula (III) includes, for example, the known compounds described in Japanese Laid-Open Patent Publication No. 23965/1978. A specific example is 2,3-dimethylmaleic anhydride.

In process (b), the starting compound of formula (I-a) is included within the compounds of the formula (I) produced by process (a).

Examples of the reducing agent used in process (b) are metal hydrides such as sodium borohydride and lithium aluminum hydride.

The compounds of the formula (I-b) used as a starting material in process (c) is included within the compounds of the formula (I) of this invention produced by process (b).

The compounds of the formula (IV) or (V) which is likewise a starting material means one based on the above definitions of $R^5$ and Hal, preferably one based on the preferred definition of $R^5$ and a chlorine atom for Hal.

The compounds of formulae (IV) and (V) are well known, and specific examples include acetyl chloride and acetic anhydride.

In practicing process (a), all inert organic solvents may be cited as suitable diluents.

Examples of such diluents include water, aromatic hydrocarbons (such as ethylene chloride, chlorobenzene, dichlorobenzene and biphenyl), ethers (such as dioxane and diphenyl ether), alcohols (such as ethanol, isopropanol, butanol, and ethylene glycol) and organic acids (such as acetic acid and propionic acid).

Process (a) can be carried out within a substantially broad temperature range, for example, between about 70° C. and about 280° C., preferably between about 80° C. and about 100° C.

Desirably, the reaction is carried out under atmospheric pressure, but it is also possible to operate under elevated or reduced pressure.

In carrying out process (a), for example, 1 mole of the compounds of the formula (II) may be reacted with about 1 to 1.2 moles of the compounds of the formula (III) in an inert organic solvent to obtain the desired compounds of the formula (I).

In the practice of process (b), water, alcohols (preferably methanol), and ethers (preferably dioxane and tetrahydrofuran) may be cited as suitable diluents.

In carrying out process (b), the desired compounds of the formula (I) can easily be obtained by reducing the compounds of the formula (I-a) with a reducing agent, exemplified hereinabove, especially preferably sodium borohydrides, as shown in a working example given hereinafter.

In the practice of process (c), aromatic hydrocarbons such as toluene, ethers such as diethyl ether and tetrahydrofuran, halogenated hydrocarbons such as dichloromethane and chloroform, and water may, for example, be cited as suitable diluents.

Process (c) can be carried out in the presence of an acid binder. Examples of the acid binder are hydrides, hydroxides, carbonates and bicarbonates of alkali metals, and tertiary amines such as triethylamine, diethylaniline and pyridine.

Process (c) may be carried out over a substantially wide temperature range, for example between about $-10°$ C. and about 100° C., preferably between about 10° C. and about 100° C.

Desirably, the reaction is carried out under atmospheric pressure, but it is also possible to operate under elevated or reduced pressure.

In carrying out process (c), the desired compounds of the formula (I) can be obtained, for example, by reacting 1 mole of the compounds of the formula (I-b) with about 1 to 1.2 moles of the compounds of the formula (IV) or (V) in an inert solvent, if desired in the presence of acid binders.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compouns according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be emplyed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the slective combating of weeds in annual cultures.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between about 0.001 and about 5 kg of active compound per hectare of soil surface, preferably between about 0.01 and about 2.5 kg per ha.

The preparation and use of the active compounds according to the invention can be seen from the following examples.

Production Examples
EXAMPLE 1

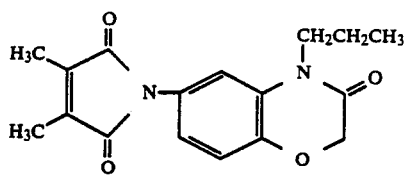 (compound No. 1)

2.27 g of 6-amino-4-propyl-2H-1,4-benzoxazin-3(4H)-one and 1.7 g of 2,3-dimethylmaleic anhydride were refluxed for 2 hours in acetic acid. After the reaction mixture was allowed to cool, 50 ml of water was added, and the precipitated crystals were collected by filtration and recrystallized from ethanol to give 1.7 g of 1-[4-propyl-2H-1,4-benzoxazin-3(4H)-on-6-yl]-3,4-dimethyl-2,5-dioxo-2,5-dihydropyrrole. m.p. 147°-149° C.

EXAMPLE 2

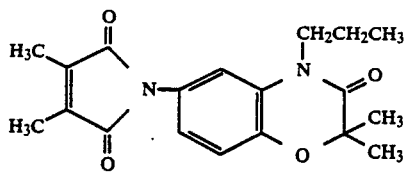 (compound No. 9)

1.83 g of 6-amino-4-propyl-2,2-dimethyl-1,4-benzoxazin-3(4H)-one and 0.96 g of 2,3-dimethylmaleic anhydride were refluxed for 2 hours in 10 ml of acetic acid. After the reaction mixture was allowed to cool, 50 ml of water was added. The precipitated crystals were collected by filtration and recrystallized with ethanol to give 1.31 g of 1-[4-propyl-2,2-dimethyl-1,4-benzoxazin-3(4)-on-6-yl]3,4-dimethyl-2,5-dioxo-2,5-dihydropyrrole. m.p. 120°-121° C.

EXAMPLE 3

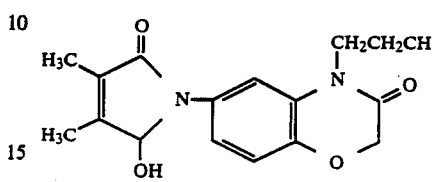 (compound No. 33)

1.15 g of 1-[4-propyl-2H-1,4-benzoxazin-3(4H)-on-6-yl]-3,4-dimethyl-2,5-dioxo-2,5-dihydropyrrole was dissolved in 100 ml of methanol, and 0.09 g of sodium borohydride was added at room temperature. The mixture was stirred at this temperature for 3 hours. One drop of acetic acid was added, and methanol was evaporated. The concentrated residue was extracted with dichloromethane, washed with water and dried. The solvent was evaporated, and the precipitated crystals were recrystallized with ethanol to give 0.8 g of 1-[4-propyl-2H-1,4-benzoxazin-3(4H)-on-6-yl]-3,4-dimethyl-2-hydroxy-5-oxo-2,5-dihydropyrrole. m.p. 124°-125° C.

The compounds of formula (I) in accordance with this invention can be prepared by the same method as in Example 1 to 3, and are shown in Table 1 together with the compounds obtained in Examples 1 to 3.

TABLE 1

| Comp. No. | A | $R^1$ | $R^2$ | $R^3$ | $R^4$ | X | mp. °C. |
|---|---|---|---|---|---|---|---|
| 1 | —C(O)— | —$C_3H_7$—n | H | H | —$CH_3$ | H | 147~149 |
| 2 | —C(O)— | —$C_3H_7$—n | —$CH_3$ | H | —$CH_3$ | H | 146~148 |
| 3 | —C(O)— | —$C_3H_7$—n | —$C_2H_5$ | H | —$CH_3$ | H | 143~144 |
| 4 | —C(O)— | —$C_3H_7$—n | —$C_3H_7$—n | H | —$CH_3$ | H | 117.5~119.5 |
| 5 | —C(O)— | —$C_3H_7$—n | —$C_4H_9$—n | H | —$CH_3$ | H | 86.5~88.5 |
| 6 | —C(O)— | —$C_3H_7$—n | —$C_6H_{11}$—n | H | —$CH_3$ | H | 95~96 |
| 7 | —C(O)— | —$C_3H_7$—n | —C₆H₅ (phenyl) | H | —$CH_3$ | H | 190~192 |

TABLE 1-continued

| Comp. No. | A | R¹ | R² | R³ | R⁴ | X | mp. °C. |
|---|---|---|---|---|---|---|---|
| 8 | −C(=O)− | −C₃H₇−n | −CH₂−C₆H₅ | H | −CH₃ | H | 120∼122 |
| 9 | −C(=O)− | −C₃H₇−n | −CH₃ | −CH₃ | −CH₃ | H | 120∼121 |
| 10 | −C(=O)− | −CH₃ | H | H | −CH₃ | H | 226∼228 |
| 11 | −C(=O)− | −C₂H₅ | H | H | −CH₃ | H | 212.5∼213.5 |
| 12 | −C(=O)− | −C₄H₉−n | H | H | −CH₃ | H | 142∼144 |
| 13 | −C(=O)− | −CH₂−CH=CH₂ | H | H | −CH₃ | H | 199∼200 |
| 14 | −C(=O)− | −CH₂−C≡CH | H | H | −CH₃ | H | 268∼270 |
| 15 | −C(=O)− | −CH₂CN | H | H | −CH₃ | H | 168∼171 |
| 16 | −C(=O)− | −CH₂OCH₃ | H | H | −CH₃ | H | 195∼198 |
| 17 | −C(=O)− | −CH₂−C₆H₅ | H | H | −CH₃ | H | 176.5∼178 |
| 18 | −C(=O)− | −CH₂COOC₂H₅ | H | H | −CH₃ | H | 129∼132 |
| 19 | −C(=O)− | −CH₂COO−C₅H₉ (cyclopentyl) | H | H | −CH₃ | H | 106∼108 |
| 20 | −C(=O)− | −CH₂−CON(CH₃)₂ | H | H | −CH₃ | H | 176−179 |
| 21 | −C(=O)− | −CH(CH₃)−CON(CH₃)₂ | H | H | −CH₃ | H | 180∼181.5 |
| 22 | −C(=O)− | −CH₂CONHCH(CH₃)₂ | H | H | −CH₃ | H | 282−290 |
| 23 | −C(=O)− | −CH₂CON(CH₃)(C₆H₅) | H | H | −CH₃ | H | 177∼178 |
| 24 | −C(=O)− | −CH₂SCH₃ | H | H | −CH₃ | H | 196−199 |

TABLE 1-continued

| Comp. No. | A | R¹ | R² | R³ | R⁴ | X | mp. °C. |
|---|---|---|---|---|---|---|---|
| 25 | -C(=O)- | -CH₂CH₂SC₂H₅ | H | H | -CH₃ | H | 142-144 |
| 26 | -C(=O)- | -C₃H₇-n | H | H | -C₂H₅ | H | 132~135 |
| 27 | -C(=O)- | -C₃H₇-n | H | H | -CH₃ | -CH₃ | 164-165 |
| 28 | -C(=O)- | -C₃H₇-n | H | H | -CH₃ | F | 112-113 |
| 29 | -C(=O)- | -C₃H₇-n | -CH₃ | H | -CH₃ | F | |
| 30 | -C(=O)- | -C₃H₇-n | H | H | -CH₃ | Cl | 122-123 |
| 31 | -C(=O)- | -CH₂OC₂H₅ | H | H | -CH₃ | H | |
| 32 | -C(=O)- | -CH₂COOCH₂CF₃ | H | H | -CH₃ | H | 130~137 |
| 33 | -C(=O)- | -CH₂SC₂H₅ | H | H | -CH₃ | H | 197-201 |
| 34 | -C(=O)- | -CH₂C≡CH | H | H | -CH₃ | F | 240-241 |
| 35 | -C(=O)- | -CH₂C≡CH | -CH₃ | H | -CH₃ | F | |
| 36 | -C(=O)- | -CH₂COOC₂H₅ | H | H | -CH₃ | F | |
| 37 | -CH(OH)- | -C₃H₇-n | H | H | -CH₃ | H | 124~125 |
| 38 | -CH(O-C(=O)CH₃)- | -C₃H₇-n | | | -CH₃ | H | 137~140 |
| 39 | -C(=O)- | -CH₂COOCH₂Si(CH₃)₃ | H | H | -CH₃ | H | 113~117 |
| 40 | -C(=O)- | -CH₂OCH₃ | H | H | -CH₃ | F | 153-154 |
| 41 | -C(=O)- | -CH₂OC₂H₅ | H | H | -CH₃ | F | |
| 42 | -C(=O)- | -CH₂OC₂H₅ | H | H | -CH₃ | H | 136-137.5 |

TABLE 1-continued

| Comp. No. | A | R¹ | R² | R³ | R⁴ | X | mp. °C. |
|---|---|---|---|---|---|---|---|
| 43 | O=C– | –CH₂CH=CH₂ | H | H | –CH₃ | F | 165–166.5 |
| 44 | O=C– | –CH₂CN | H | H | –CH₃ | F | 236–239 |
| 45 | O=C– | –CH₂–COOCH₂Si(CH₃)₃ | H | H | –CH₃ | F | 123–125 |
| 46 | O=C– | H | H | H | –CH₃ | H | 238–242 |
| 47 | O=C– | –CH₂–C≡CH | H | H | –CH₃ | –CH₃ | 255–256.5 |
| 48 | O=C– | –CH₂–C≡CH | H | H | –CH₃ | Cl | 249–251 |
| 49 | O=C– | –CH₂–CH=CH–CH₃ | H | H | –CH₃ | H | 146–147.5 |
| 50 | O=C– | –CH(CH₃)–CH=CH₂ | H | H | –CH₃ | H | 106–110 |
| 51 | O=C– | –CH₂–C(CH₃)=CH₂ | H | H | –CH₃ | H | 107–123 |
| 52 | O=C– | –CH₂–CH₂–CH=CH₂ | H | H | –CH₃ | H | 122–133 |
| 53 | O=C– | –CH(CH₃)–CN | H | H | –CH₃ | H | 142–145 |
| 54 | O=C– | –CH₂–CH₂–O–C₂H₅ | H | H | –CH₃ | H | 118–119 |
| 55 | O=C– | –CH₂–O–CH₂–C≡CH | H | H | –CH₃ | H | 185–190 |
| 56 | O=C– | –C₃H₇–n | –CH₂–C₆H₄–Cl (4-Cl) | H | –CH₃ | H | 109–111 |
| 57 | O=C– | –CH₂–CH=CH₂ | –CH₂–C₆H₄–Cl (4-Cl) | H | –CH₃ | H | 92–102 |
| 58 | O=C– | –CH₂–C≡CH | –CH₂–C₆H₄–Cl (4-Cl) | H | –CH₃ | H | 115–125 |

TABLE 1-continued structure with R⁴, A, N, R¹, R², R³, X substituents on the described scaffold

| Comp. No. | A | R¹ | R² | R³ | R⁴ | X | mp. °C. |
|---|---|---|---|---|---|---|---|
| 59 | −C(=O)− | −CH₂−C₆H₅ | H | H | −CH₃ | F | |
| 60 | −C(=O)− | −CH₂COO−cyclopentyl(H) | H | H | −CH₃ | F | |
| 61 | −C(=O)− | −CH₂SCH₃ | H | H | −CH₃ | F | |
| 62 | −C(=O)− | −CH₂SC₂H₅ | H | H | −CH₃ | F | |
| 63 | −CH(OH)− | −C₃H₇−n | H | H | −CH₃ | F | |
| 64 | −CH(OH)− | −CH₂CH=CH₂ | H | H | −CH₃ | F | |
| 65 | −CH(OH)− | −CH₂C≡CH | H | H | −CH₃ | F | |
| 66 | −CH(O−C(=O)CH₃)− | −CH₂CH=CH₂ | H | H | −CH₃ | F | |
| 67 | −CH(O−C(=O)CH₃)− | −CH₂C≡CH | H | H | −CH₃ | F | |
| 68 | −C(=O)− | H | H | H | −CH₃ | F | |

Biological tests

Comparative compound (E-1)

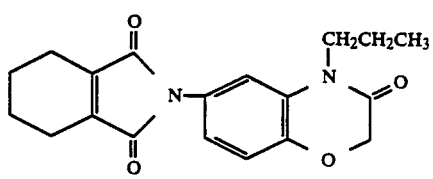

(the compound described in Japanese Laid-Open Patent Publication No. 30586/1986)

EXAMPLE 4

Test on weeds in a flooded paddy by water surface application:

Preparation of an active compound formulation
Carrier: 5 parts by weight of acetone
Emulsifier: 1 part by weight of benzyloxy polyglycol ether A formulation of an active compound was obtained as an emulsifiable concentrate by mixing 1 part by weight of the active compound with the above-mentioned amounts of the carrier and the emulsifying agent. A predetermined amount of the formulation was diluted with water.

Testing method

Paddy soil was filled in pots (1/2,000 are; 25×20×9 cm), and rice seedlings (variety: "Nihonbare") in the 2.5-leaf stage (15 cm tall) were transplanted at two places per pot each as a stock of three seedlings. Seeds of barnyard grass (*Echinochloa oryzicola* Vasing.), umbrella plant (*Cyperus difformis* L.), monochoria (*Monochoria vaginalis,* and annual broad-leaved weeds [false pimpernel (*Lindernia pyxidaria* L.), *Rotala indica,* American waterwort (*Elatine triandra*), red stem (*Ammannia multiflora* Roxburgh) and *Dopatrium junceum*

Hamilton] were sown and the pots were maintained wet. Two days later, the pots were flooded to a depth of about 2 to 3 cm. Five days after the transplantation of the seedlings, the compound of this invention, in the form of an emulsifiable concentrate as prepared above, was applied to the water surface by a pipette in a predetermined amount. Thereafter, the flooded condition of about 3 cm was maintained, and four weeks after the chemical treament, the herbicidal effect and the phytotoxicity to rice were evaluated and rated on the scale of 0 to 5 as follows:

Herbicidal effect (evaluated by a weed killing ratio based on a non-treated lot):
5: at least 95% (withered)
4: at least 80% but less than 95%
3: at least 50% but less than 80%
2: at least 30% but less than 50%
1: at least 10% but less than 30%
0: less than 10% (no effect)

Phytotoxicity to rice (evaluated based on a non-treated lot):
5: at least 90% (fatal injury)
4: at least 50% but less than 90%
3: at least 30% but less than 50%
2: at least 10% but less than 30%
1: more than 0 but less than 10%
0: 0% (no phytotoxicity)

The test results are shown in Table 2 by typical examples.

TABLE 2

| Compound No. | Amount of the active ingredient (kg/ha) | Herbicidal effect | | | | Phyto-toxicity Rice |
|---|---|---|---|---|---|---|
| | | Barnyard grass | Umbrella plant | Monochoria | Broad-leaved weeds | |
| 1 | 0.5 | 5 | 5 | 5 | 5 | 1 |
| | 0.25 | 4 | 5 | 5 | 5 | 0 |
| | 0.125 | 4 | 5 | 4 | 4 | 0 |
| Comparison E-1 | 0.5 | 5 | 5 | 5 | 5 | 4 |
| | 0.25 | 3 | 5 | 4 | 4 | 3 |
| | 0.125 | 1 | 4 | 2 | 2 | 2 |

EXAMPLE 5

Test on upland weeds by soil treatment before emergence:

In a greenhouse, soybean seeds were sown in 500 cm² pots filled with upland farm soil, and soil containing seeds of barnyard grass (*Echinochloa crus-galli*), livid amaranth (*Amaranthus lividus* L.) and goosefoot (*Chenopodium album* L.) was put over the soil in the pots in a depth of 1 cm.

One day after the sowing, a test chemical in a predetermined concentration, prepared as in Example 4, was uniformly sprayed over the surface layer of the soil in each of the test pots.

Four weeks after the spraying, the herbicidal effect and the phytotoxicity to crops were examined on the same standards as in Example 4. The results are shown in Table 3 by typical examples.

TABLE 3

| Compound No. | Amount of the active ingredient (kg/ha) | Herbicidal effect | | | Phyto-toxicity Soybeans |
|---|---|---|---|---|---|
| | | Barn-yard grass | Livid amaranth | Goose-foot | |
| 1 | 0.5 | 5 | 5 | 5 | 1 |
| | 0.25 | 4 | 5 | 5 | 0 |
| | 0.125 | 3 | 5 | 5 | 0 |
| Comparison | 0.5 | 4 | 5 | 5 | 4 |

TABLE 3-continued

| Compound No. | Amount of the active ingredient (kg/ha) | Herbicidal effect | | | Phyto-toxicity Soybeans |
|---|---|---|---|---|---|
| | | Barn-yard grass | Livid amaranth | Goose-foot | |
| E-1 | 0.25 | 3 | 5 | 5 | 3 |
| | 0.125 | 3 | 4 | 3 | 3 |

EXAMPLE 6

Test on upland farm weeds by foliar treatment

In a greenhouse, soybean seeds were sown in 500 cm² pots filled with upland farm soil, and soil containing seeds of barnyard grass (*Echinochloa crus-galli*), livid amaranth (*Amaranthus lividus* L.) and goosefoot (*Chenopodium album* L.) was put over the soil in the pots in a depth of 1 cm.

After sowing, the plants were grown for 14 days and a test chemical in a predetermined concentration, prepared as in Example 4, was uniformly sprayed over the test plants in each of the test pots.

Four weeks after the spraying, the herbicidal effect and the phytotoxicity to crops were examined on the same standards as in Example 4. The results are shown in Table 4 by typical examples.

TABLE 4

| Compound No. | Amount of the active ingredient (kg/ha) | Herbicidal effect | | | Phyto-toxicity Soybeans |
|---|---|---|---|---|---|
| | | Barn-yard grass | Livid amaranth | Goose-foot | |
| 1 | 0.5 | 5 | 5 | 5 | 2 |
| | 0.25 | 5 | 5 | 5 | 1 |
| | 0.125 | 4 | 5 | 5 | 0 |
| Comparison E-1 | 0.5 | 5 | 5 | 5 | 5 |
| | 0.25 | 5 | 5 | 5 | 4 |
| | 0.125 | 4 | 5 | 5 | 3 |

It will be understood that the specification and examples are illustrative but not limitative of the present invention and that other embodiments within the spirit and scope of the invention will suggest themselves to those skilled in the art.

We claim:

1. A dialkylmaleimide of the formula $$\begin{array}{c}\text{(I)}\end{array}$$

[structural formula showing: $R^4$ groups on a carbon double bond connected to A, then to a benzene ring with X substituent, connected to N of a ring bearing $R^1$, with C=O groups and $R^2$, $R^3$ substituents]

wherein
A is

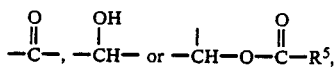

R¹ is a hydrogen atom, an alkyl group, an alkenyl group, an alkynyl group, an aralkyl group, an alkoxyalkyl group, a cyanoalkyl group, a trialkylsilylalkyl group, an alkylthioalkyl group or the group

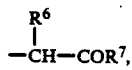

R² is a hydrogen atom or an alkyl, aryl or aralkyl group,
R³ is a hydrogen atom or an alkyl group,
R⁴ is an alkyl group,
R⁵ is an alkyl or aryl group,
R⁶ is a hydrogen atoms or an alkyl group
R⁷ is an alkoxy, cycloalkoxy, haloalkoxy, alkylamino, dialkylamino, N-alkyl-N-arylamino or trialkylsilylalkoxy group, and
X is a hydrogen atom, a halogen atom or an alkyl group.

2. A compound according to claim 1, in which
R¹ is a hydrogen atom, an alkyl group having 1 to 4 carbon atoms, an alkenyl group having 2 to 4 carbon atoms, an alkynyl group having 2 to 4 carbon atoms, a benzyl group, an alkoxyalkyl group having 2 to 6 carbon atoms in total, a cyanomethyl group, a trimethylsilylmethyl group, an alkylthioalkyl group having 2 to 6 carbon atoms in total or the group

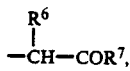

R² is a hydrogen atom, an alkyl group having 1 to 6 carbon atoms, a phenyl group or a benzyl group,
R³ is a hydrogen atom or an alkyl group having 1 to 4 carbon atoms,
R⁴ is an alkyl group having 1 to 4 carbon atoms,
R⁵ is an alkyl group having 1 to 4 carbon atoms or a phenyl group,
R⁶ is a hydrogen atom or an alkyl group having 1 to 2 carbon atoms,
R⁷ is an alkoxy group having 1 to 4 carbon atoms, a cycloalkoxy group having 3 to 7 carbon atoms, a haloalkoxy group having 1 to 4 carbon atoms, an alkylamino or dialkylamino group having 2 to 6 carbon atoms in total, an N-(C₁-C₄)alkyl-N-phenylamino group, or a trimethylsilylmethoxy group, and
X is a hydrogen atom, a fluorine atom, a chlorine atom, a bromine atom, a methyl group or an ethyl group.

3. A compound according to claim 1, in which
R¹ is a hydrogen atom, a methyl, ethyl, propyl, allyl, propargyl, benzyl, methoxymethyl, cyanomethyl, trimethylsilylmethyl, methylthiomethyl or 2-ethylthioethyl group or the group

R² is a hydrogen atom or a methyl, ethyl, n-propyl, n-butyl, n-hexyl, phenyl or benzyl group,
R³ is a hydrogen atom or a methyl group,
R⁴ is a methyl group,
R⁵ is a methyl, ethyl or phenyl group,
R⁶ is a hydrogen atom or a methyl group,
R⁷ is a methoxy, ethoxy, cyclopentyloxy, cyclohexyloxy, trifluoroethoxy, isopropylamino, dimethylamino, N-methyl-N-phenylamino or trimethylsilylmethoxy group, and
X is a hydrogen or fluorine atom.

4. A compound according to claim 1, wherein such compound is 1-[4-propyl-2H-1,4-benzoxazin-3(4H)-on-6-yl]-3,4-dimethyl-2,5-dioxo-2,5-dihydropyrrole of the formula

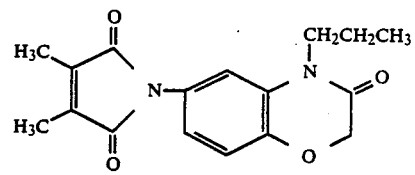

5. A compound according to claim 1, wherein such compound is 1-[4-allyl-2H-1,4-benzoxazin-3(4H)-on-6-yl]-3,4-dimethyl-2,5-dioxo-2,5-dihydropyrrole of the formula

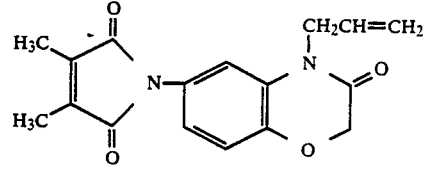

6. A compound according to claim 1, wherein such compound is 1-[4-propargyl-2H-1,4-benzoxazin-3(4H)-on-6-yl]-3,4-dimethyl-2,5-dioxo-2,5-dihydropyrrole of the formula

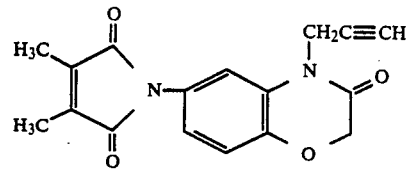

7. A compound according to claim 1, wherein such compound is 1-[4-propyl-2-methyl-1,4-benzoxazin-3(4H)-on-6yl]-3,4-dimethyl-2,5-dioxo-2,5-dihydropyrrole of the formula

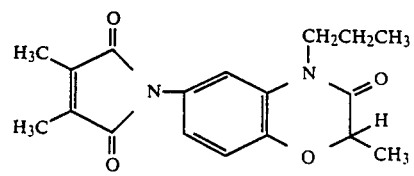

8. A compound according to claim 1, wherein such compound is 1-[4-propyl-2,2-dimethyl-1,4-benzoxazin-3(4H)-on-6-yl]-3,4-dimethyl-2,5-dioxo-2,5-dihydropyrrole or the formula

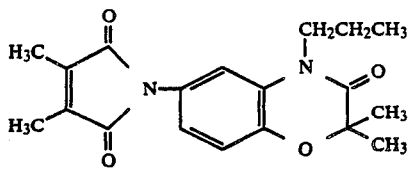

9. A herbicidal composition comprising a herbicidally effective amount of a compound according to claim 1 and a diluent.

10. A method of combating unwanted vegetation which comprises applying to such vegetation or to a locus from which it is desired to exclude such vegetation a herbicidally effective amount of a compound according to claim 1.

11. The method according to claim 10, wherein such compound is
1-[4-propyl-2H-1,4-benzoxazin-3(4H)-on-6-yl]-3,4-dimethyl-2,5-dioxo-2,5-dihydropyrrole,
1-[4-allyl-2H-1,4-benzoxazin-3(4H)-on-6-yl]-3,4-dimethyl-2,5-dioxo-2,5-dihydropyrrole,
1-[4-propargyl-2H-1,4-benzoxazin-3(4H)-on-6-yl]-3,4-dimethyl-2,5-dioxo-2,5-dihydropyrrole,
1-[4-propyl-2-methyl-1,4-benzoxazin-3(4H)-on-6yl]-3,4-dimethyl-2,5-dioxo-2,5-dihydropyrrole, or
1-[4-propyl-2,2-dimethyl-1,4-benzoxazin-3(4H)-on-6-yl]-3,4-dimethyl-2,5-dioxo-2,5-dihydropyrrole.

* * * * *